US00PP29151P3

(12) United States Plant Patent
Stuff

(10) Patent No.: US PP29,151 P3
(45) Date of Patent: Mar. 27, 2018

(54) HOP PLANT NAMED 'STUFF'

(50) Latin Name: ***Humulus lupulus* L.**
Varietal Denomination: STUFF

(71) Applicant: Stuff Seed Company, Ft. Loudon, PA (US)

(72) Inventor: Melissa Stuff, Mercerburg, PA (US)

(73) Assignee: Stuff Seed Company, Ft. Loudon, PA (US)

( * ) Notice: Subject to any disclaimer, the term of this patent is extended or adjusted under 35 U.S.C. 154(b) by 4 days.

(21) Appl. No.: 14/756,307

(22) Filed: Aug. 25, 2015

(65) Prior Publication Data

US 2017/0064893 P1 Mar. 2, 2017

(51) Int. Cl.
*A01H 5/02* (2006.01)

(52) U.S. Cl.
USPC ..... Plt./236

(58) Field of Classification Search
USPC ..... Plt./236
CPC ..... A01H 5/02
See application file for complete search history.

*Primary Examiner* — Kent L Bell
(74) *Attorney, Agent, or Firm* — Cooley LLP

(57) ABSTRACT

The present invention provides a new and distinct hop plant variety designated as 'STUFF'. The cones of 'STUFF' mature in late August, and yield a crop of 1600 to 2000 pounds per acre. 'STUFF' is used for its unique aromatic quality, resistance to powdery mildew, high alpha acid content, dual purpose use and exceptional yield.

8 Drawing Sheets

Latin name of genus and species: *Humulus hipulus* L.
Varietal denomination: 'STUFF' (or 'Stuff').

BACKGROUND OF THE INVENTION

*Humulus hipulus* (common hop or hop) is a species of flowering plant in the Cannabaceae family, native to Europe, western Asia and North America. It is a dioecious, perennial, herbaceous climbing plant which sends up new shoots in early spring and dies back to a cold-hardy rhizome in autumn.

*Humulus hipulus* is a main ingredient of many beers, and as such is widely cultivated for use by the brewing industry. The fragrant flower cones impart bitterness and flavor, and also have preservative qualities.

The flowers (cones) of the female hop plant are used in the marking of beverage, especially beer, as a flavoring and processing component. It contributes to the bitterness and aroma in beer as well as foam quality, flavor, and taste stability.

Hops are native to the temperate zones of the northern hemisphere. They are found wild in certain parts of North America. Commercial hops are generally grown between the 30th and 50th parallel north or south latitude and at various altitudes.

SUMMARY OF THE INVENTION

The present invention relates to a new and distinct hop plant designated as 'STUFF'. This new variety was discovered by the inventor in a cultivated area of a family farm in Fannettsburg, Pa. 17224.

The new variety of 'STUFF' was asexually reproduced by the inventor at Mercersburg, Pa. by rhizome divisions. Asexual propagules from the original source have been tested in the greenhouse and growing fields. The properties of this variety were found to be transmissible by such asexual reproduction. The cultivar is stable and reproduces true to type in successive generations of asexual reproduction.

The parents of the new variety of hops are unknown since it was discovered in a cultivated area and not the result of a controlled cross between two known parents. Leaf samples of the 'STUFF' hop variety were genotyped using 20 hops SSR marker loci along with leaf samples of the following well known and established commercial hop varieties: 'Nugget', 'Mt. Hood', 'Cascade', 'Centennial', 'Willamette', 'Galena', 'Chinook' and 'Sterling'. Although the genotypic data that was generated from the total of 38 samples is not robust enough to draw definitive conclusions, it indicated that the 'STUFF' hop variety is more closely related to 'Sterling' and/or 'Cascade' than to the other varieties that were sampled. Both 'Sterling' and 'Cascade' are unpatented.

The following traits in combination distinguish hop plant 'STUFF' from the known hop plants. In the following description, color references are made to The Royal Horticultural Society Colour Chart, 1995 Edition, except where general terms of ordinary dictionary significance are used.

DESCRIPTION OF THE DRAWINGS

The accompanying color photographs depict various characteristics of the 'STUFF' hop plant as nearly true as possible to make color reproductions. The colors of these illustrations may vary with lighting conditions and, therefore, color characteristics of this new variety should be determined with reference to the observations described herein, rather than from these illustrations alone.

DETAILED BOTANICAL DESCRIPTION

Figure 1:
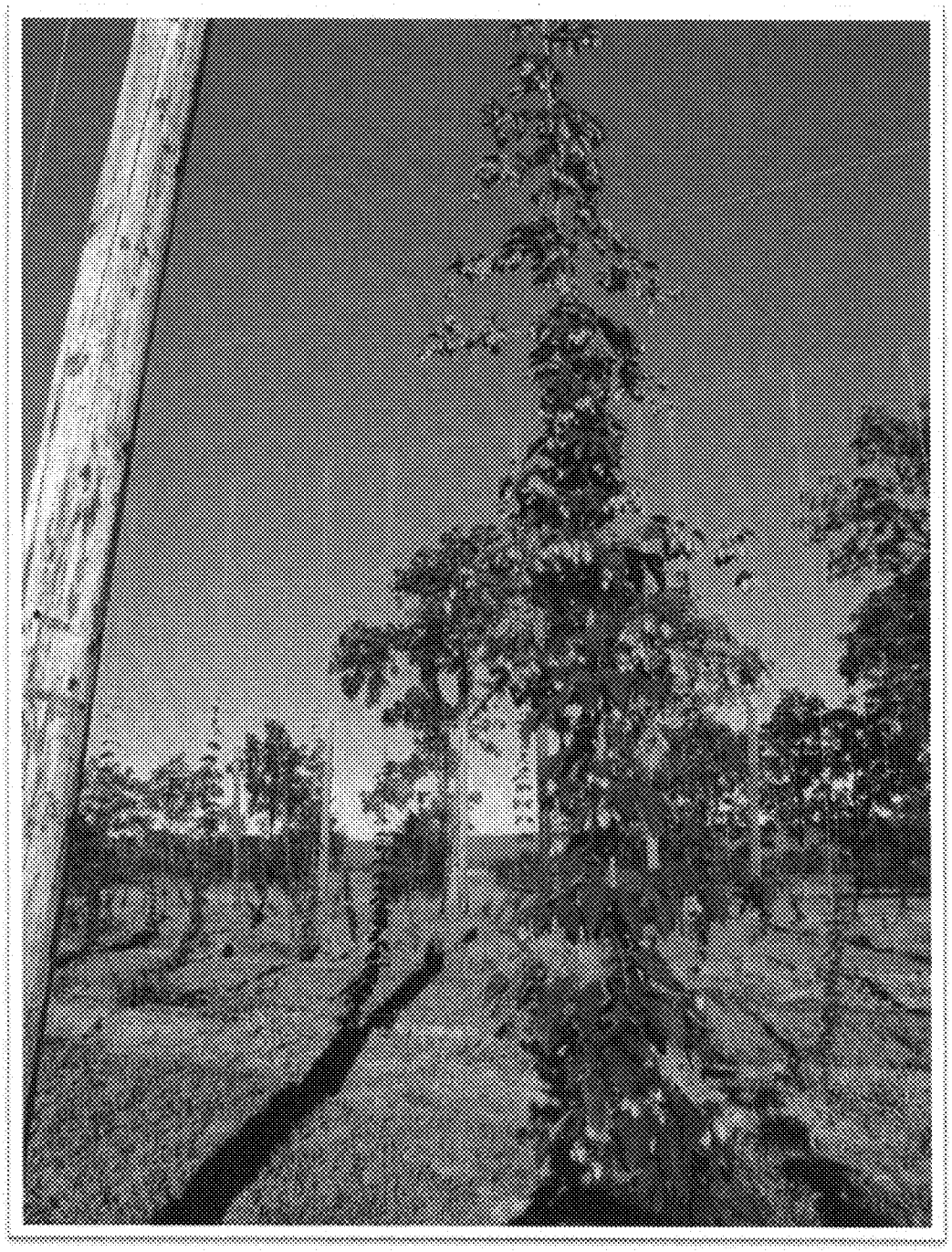
FIG. 1 shows mature 1-year old 'STUFF' plant growing on trellis.
Figure 2:
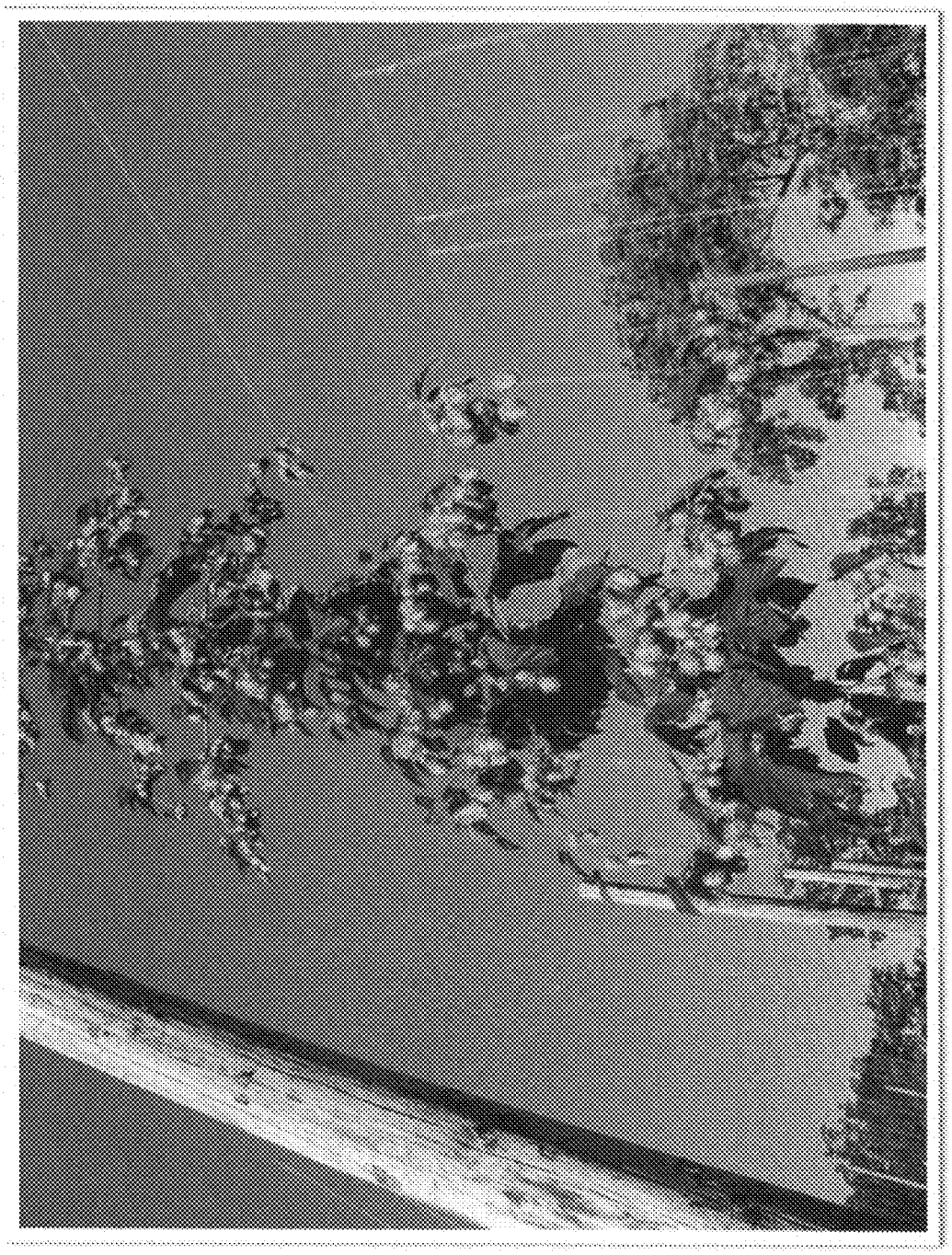
FIG. 2 shows 'STUFF' plant having cones.
Figure 3:
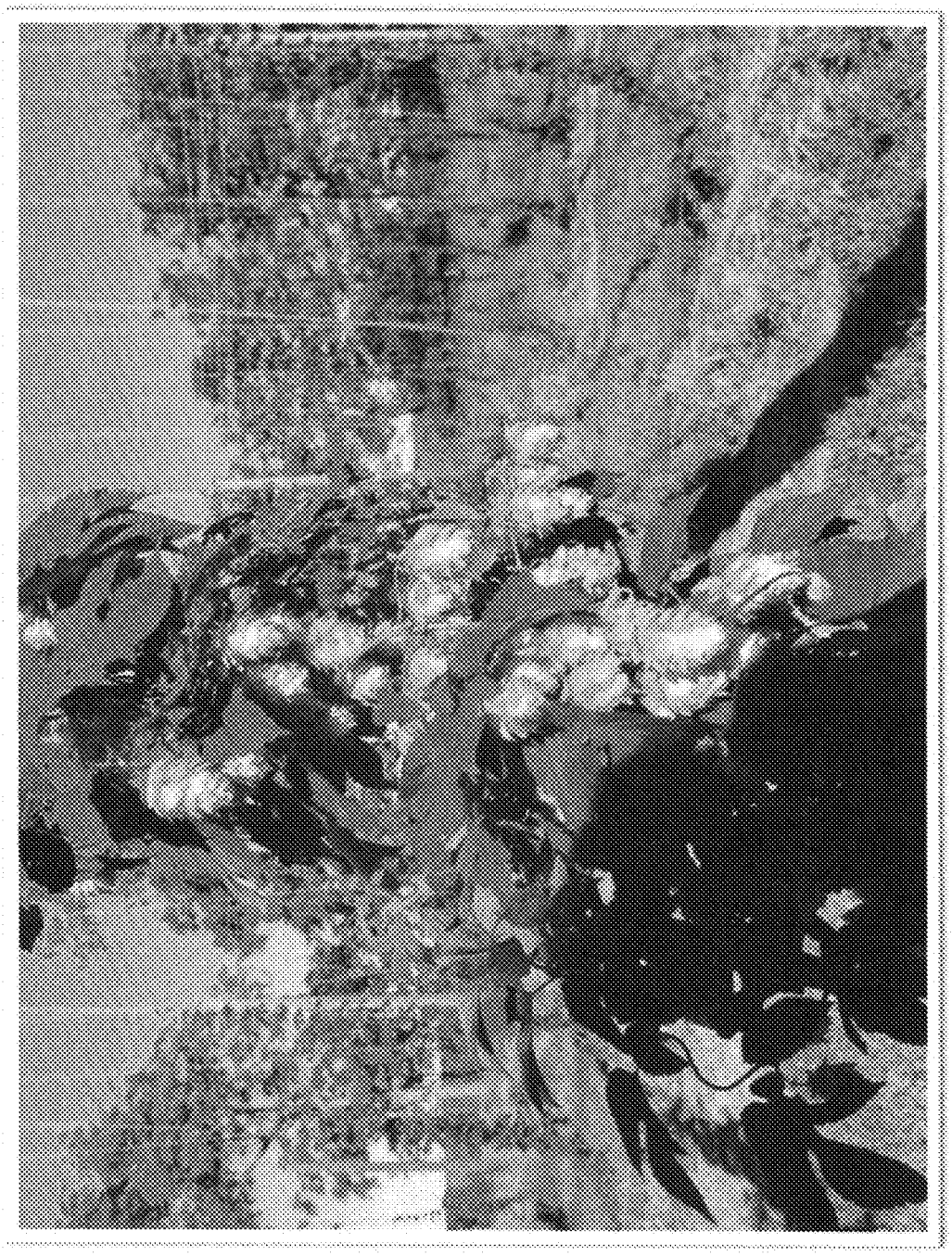
FIG. 3 shows details of cones of the 'STUFF' plant.
Figure 4:
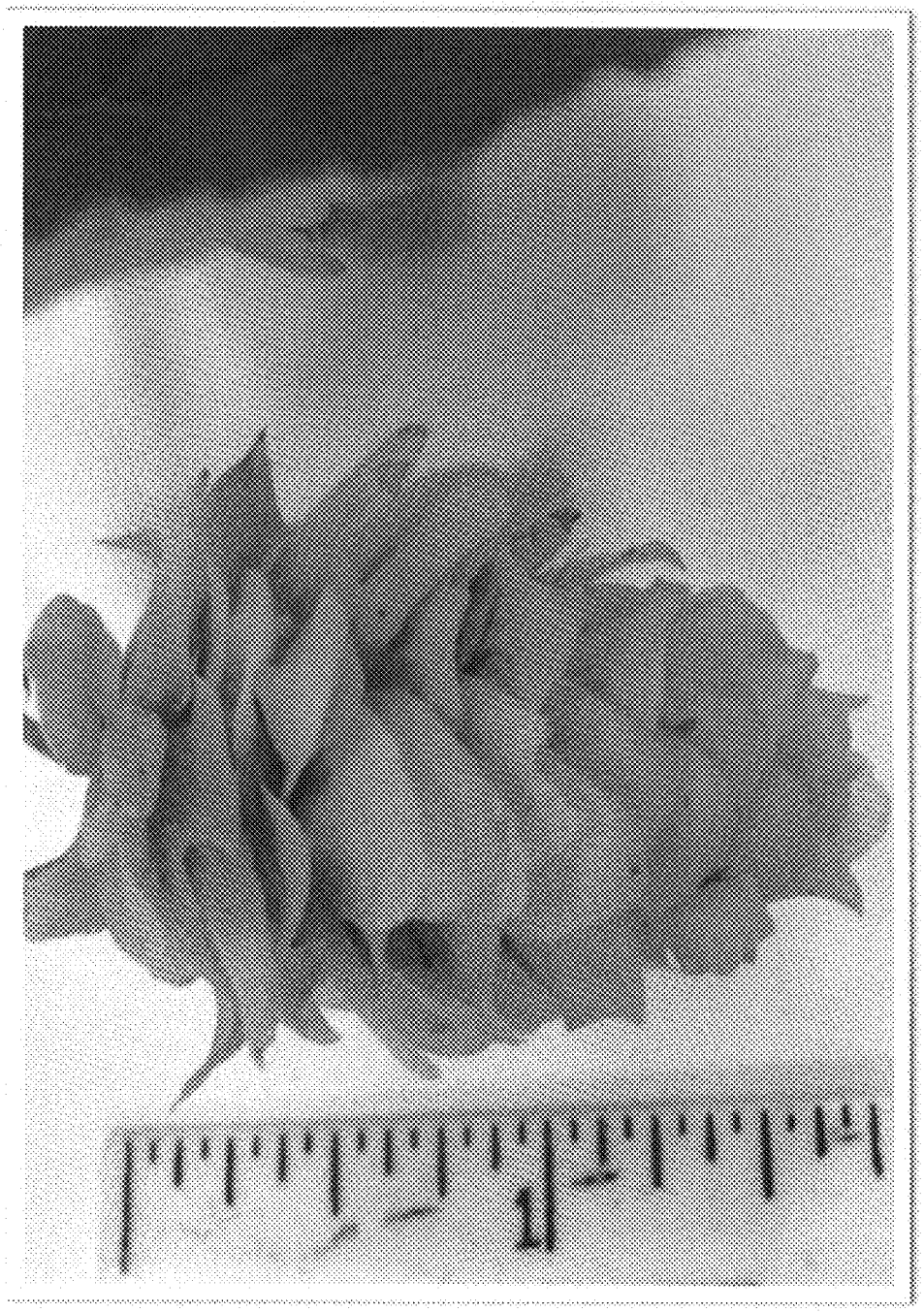
FIG. 4 shows a mature cone of the 'STUFF' hop plant.
Figure 5:
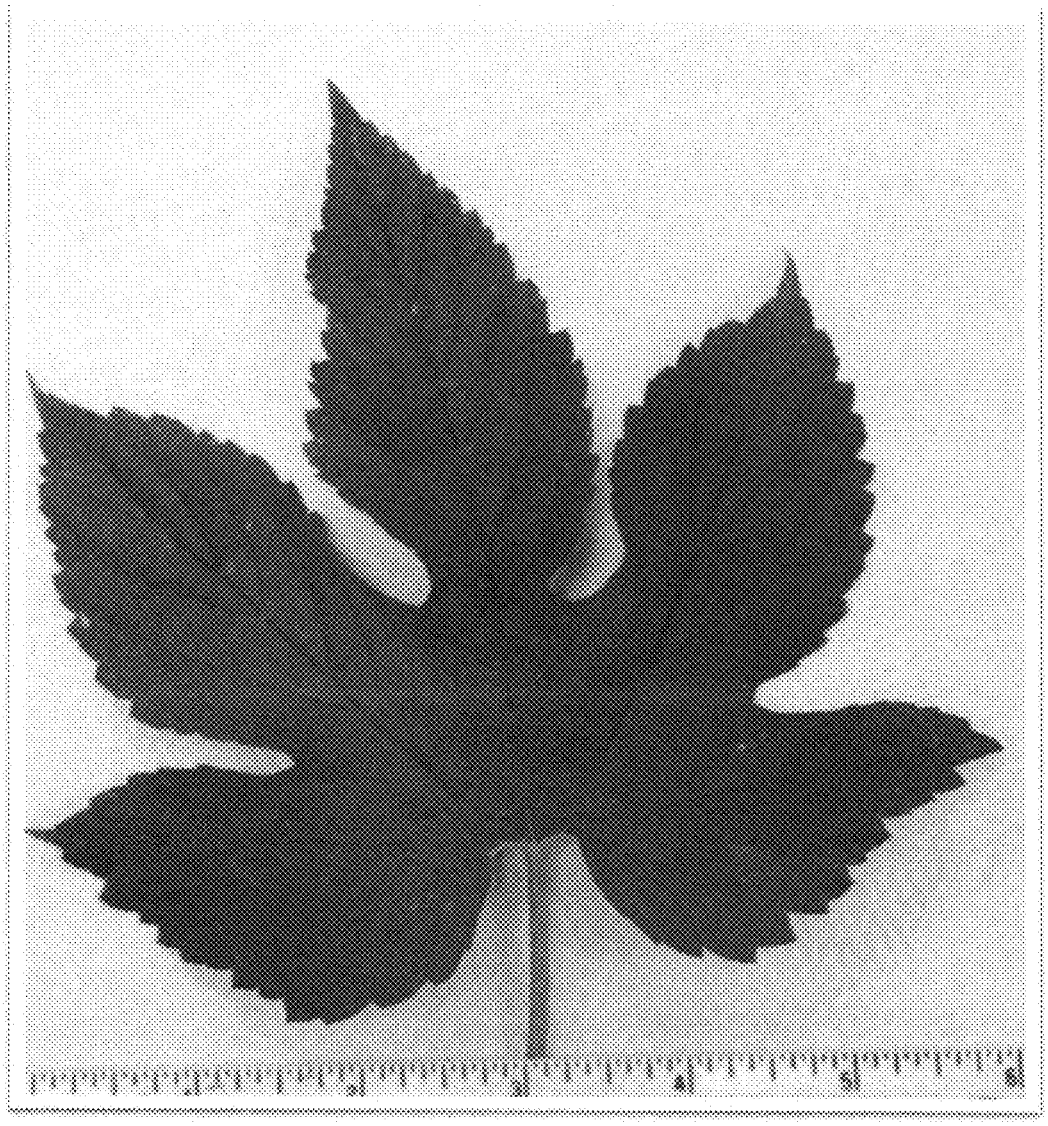
FIG. 5 shows a mature leaf of the 'STUFF' hop plant.
Figure 6:
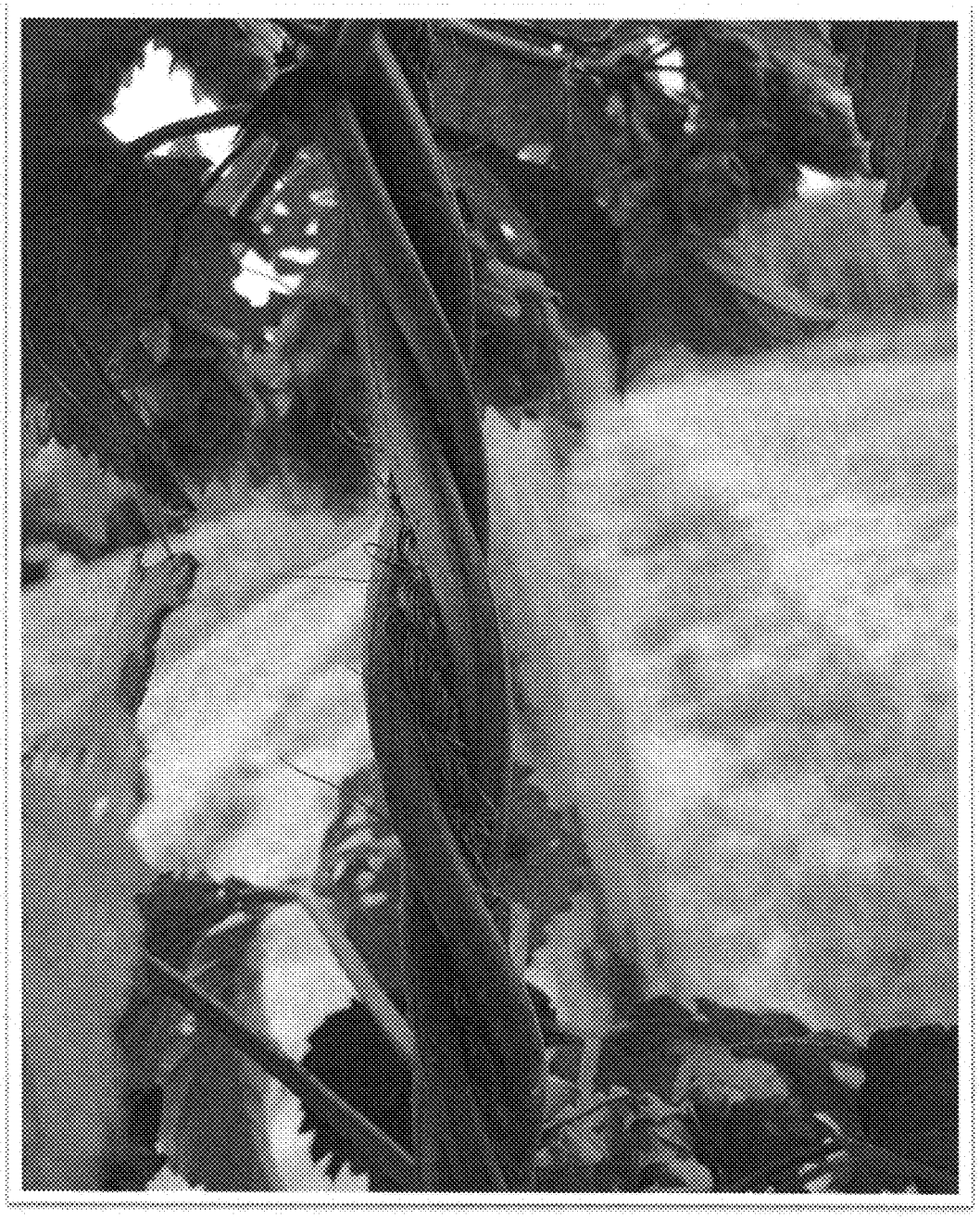
FIG. 6 shows a mature stem of the 'STUFF' hop plant.
Figure 7:
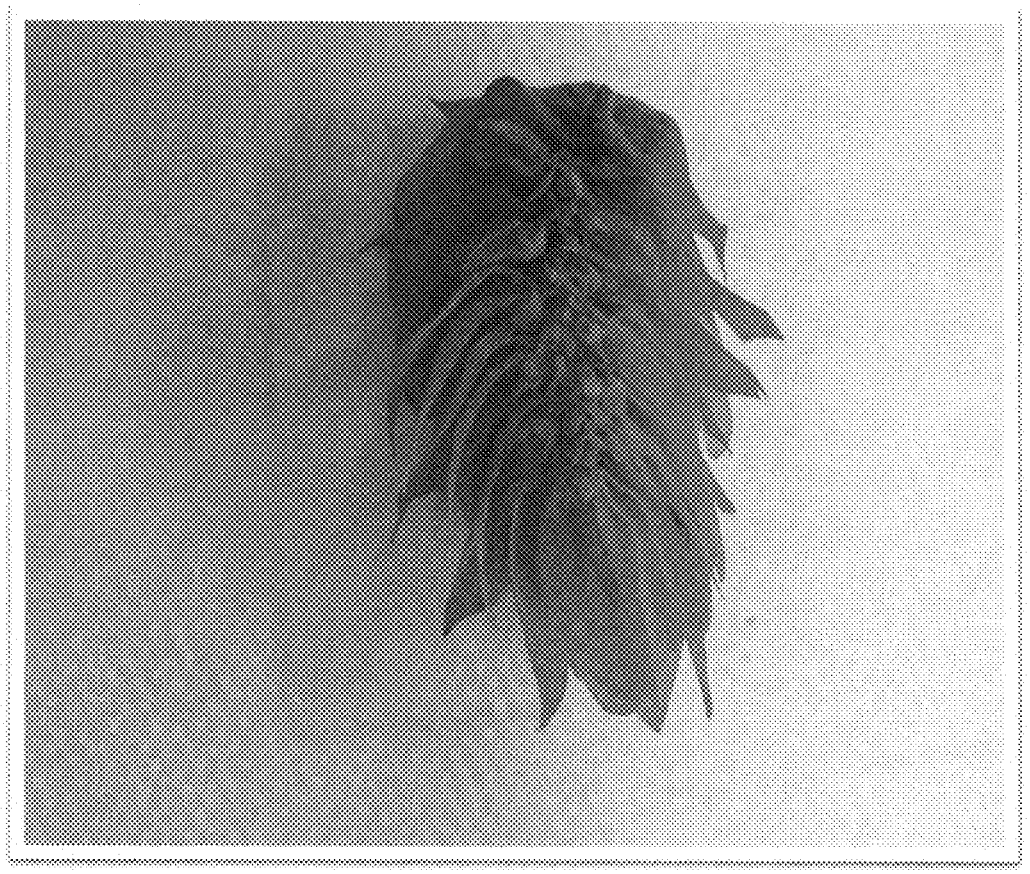
FIG. 7 shows cross-section of a mature cone of the 'STUFF' hop plant.
Figure 8:
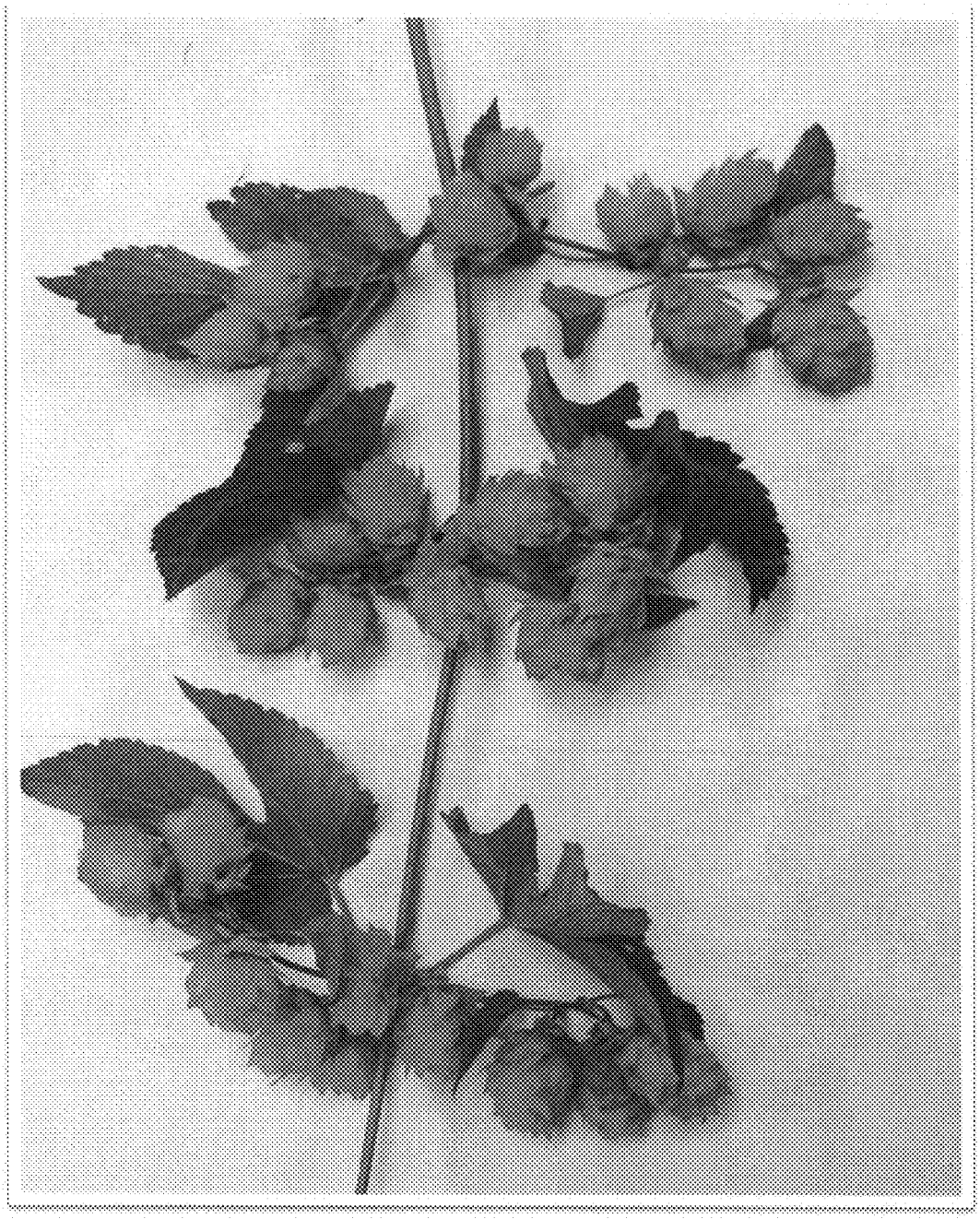
FIG. 8 shows group of cluster-like cones from lateral branches of the 'STUFF' hop plant.

This invention relates to a new and distinctive hop plant cultivar designated as 'STUFF'. 'STUFF' is hardy, perennial plant which produces annual vines from a permanent root stock (crown). It is in flower from July to September, and the seeds ripen from September to October.

'STUFF' has not been observed under all possible environmental conditions, and the phenotype may vary significantly with variations in environment. The following observations, measurements, and comparisons describe this plant as grown at Pennsylvania, when grown in the field, unless otherwise noted. As stated above, the color determination is in accordance with The Royal Horticultural Society Colour Chart, 1995 Edition, except where general color terms of ordinary dictionary significance are used.

'STUFF' has been compared to, and can be distinguished from the common variety, 'CASCADE':

TABLE 1

| 'STUFF' | 'CASCADE' |
|---|---|
| Much larger leaves | Medium leaf size |
| Many more lateral branches | Few lateral branches |
| Much more aggressive growth | Medium growth rate |
| Many more cones/yield | Average yield |
| Striped Mature Bine | No stripe on Mature Bine |
| Hops on laterals grow in clusters | Hops on laterals grow individually |
| Easy to Propagate from cutting | Easy to propagate from cutting |

Attempts to propagate the 'STERLING' hop variety have shown that it is much harder to propagate than the new 'STUFF' hop variety.

Dry cones of the 'STUFF' hop variety were analyzed for brewing values. Utilizing a UV Spectrophotometer, this test determined that 'STUFF' had a 13.2 value for Alpha acids, a 6.1 value for Beta acids, and a Hop Storage Index (HSI) of 0.235.

DETAILED BOTANICAL DESCRIPTION OF THE VARIETY

The following description is based on observations made during growing season at Mercersburg, Pa. Observations were made on one year old plants, planted in June. It should be understood that the characteristics described will vary somewhat depending upon age of plant, cultural practices and climatic conditions, and can vary with location and season. Quantified measurements are expressed as an average of measurements taken from a number of individual plants of the new variety. The measurements of any individual plant or any groups of plants, of the new variety may vary from the stated average.

Species: *Humulus lupulus*.

Ploidy: Diploid.

Use: Brewing.

Disease susceptibility: 'STUFF' is resistant to powdery mildew.

Pest susceptibility: 'STUFF' is not resistant to normal infestations of hop aphid and normal infestations of two-spotted spider mite.

Harvest date: August-September.

Crop yield: 2000 pounds per acre.

Plant: Vigorous, Perennial Climbing Vine.

Plant shape: Columnar.

Growth rate: Fast, reaching 25' in one growing season.

Branching habit: Opposite, with laterals reaching an average of 10.5 inches (Some as long as 33').

Plant diameter: 21 inches.

Regional adaptation: Adapted to US. Zones 6 and 6a.

Life expectancy: 20 years.

Bine:

- *Color*.—Ocher green 152a.
- *Stripe*.—Present, purple-brown color 183a.
- *Stipule direction*.—Downward and forked.
- *Stipule color*.—Yellow green 143b.
- *Stipule number per bine*.—15 to 19 pair (dicotyledons) per bine.
- *Bine diameter*.—7.66 mm at base; 4.73 mm at 6 feet; 6.27 mm at 9 feet.
- *Bine length*.—23 feet at mid/late season.
- *Bine inter-node length*.—Average 9".

Lateral branch:

- *Length*.—10.5".
- *Diameter*.—5.½ mm.
- *Internode length*.—9-10 inches/average.
- *Texture*.—Pubescent.
- *Strength*.—Strong.
- *Color*.—Fully Developed: Upper surface: Yellow green 144a Lower surface: Yellow green 144a.

Leaf:

- *Arrangement*.—Opposite.
- *Shape*.—Palmately Compound and coarsely toothed to Cordate.
- *Average length of mature leaf*.—14.6 cm.
- *Average width of mature leaf*.—15.24 cm.
- *Color of mature leaf upper surface*.—Yellow green 139a.
- *Color of mature leaf lower surface*.—Yellow green 137b.
- *Color of immature leaf upper surface*.—Yellow green 139a.
- *Color of immature leaf lower surface*.—Yellow green 137b.
- *Number of lobes*.—1-5.
- *Margin*.—Serrate.
- *Serrations per inch*.—4-5.
- *Average petiole length (mature)*.—54.60 mm.
- *Petiole color at base*.—Yellow green 143c.
- *Petiole diameter*.—9.52 mm.
- *Petiole color*.—Green RHS color 146C with redish/purplish, RHS color 183A, stripes on upper side of petiole with some green showing through.
- *Venation*.—Palmate.
- *Vein color*.—Yellow green 144c.
- *Leaf apex and base description*.—Palmate lobed with upper surface being rough and bottom surface smooth.

Cone:

- *Average weight*.—1 gram.
- *Average length*.—44.45 mm.
- *Average diameter*.—16.74 mm.
- *Bract tip color*.—Yellow green 145b.

*Bract base color*.—Yellow green 145a.
*Bracteole color*.—Yellow green 149b.
*Cone shape*.—Ovoid.
*Bract shape*.—Ovate.
*Bract tip shape*.—Cuspidate to Attenuate.
*Bract tip position*.—Slightly everted.
*Bract length*.—16 mm.
*Bract width*.—8 mm.
*Bract margin*.—Entire with an obtuse tip.
*Bract base*.—Rounded.
*Bracteole shape*.—Ovate.
*Bracteole length*.—16 mm.
*Bracteole width*.—8 mm.
*Bracteole apex*.—Acute.
*Pickability*.—Good.
*Aroma*.—Pine, grass, citrus, tropical, floral.
*Growth pattern*.—Cluster-like/average 10 cones to cluster on laterals.
*Lupulin gland per cone*.—Moderate. The cones contain numerous lupulin glands and are hard to quantify. The number also vary from year to year based upon environmental and weather factors.
*Lulupin gland shape*.—Sphere like.
*Lulupin gland color*.—RHS 13A.

Analytical characteristics:
*Alpha acid* (*as % of cone weight*).—13.2% (ASBC spectrophoto-metric method).
*Cohumulone % of alpha acids*.—39.4%.
*Beta acid* (*as % of cone weight*).—6.1% (ASBC spectrophoto-metric method).
*Colupulone % of beta acids*.—66.3%.
*Hop storage index*.—0.235.
*Essential oil profile*.—Essential Oil Profile of 'STUFF' — Gas Chromatogram. A-pinene — 0.03% of total oil. B-pinene — 0.22% of total oil. Myrcene — 15.92% of total oil. Limonene — 0.12% of total oil. 2-methyl-butyl isobutyrate — 0.85% of total oil. Linalool — 0.35% of total oil. Caryophyllene — 21.04% of total oil. Farnesene — 0.28% of total oil. Humulene — 32.73% of total oil. Citral — 2.26% of total oil. Geraniol — 0.06% of total oil. Geranyl Acetate — 0.02% of total oil. Citronellol — 2.52% of total oil. Nerol — 0.25% of total oil. B-lonene — 0.04% of total oil. Carophyllene Oxide — 0.17% of total oil.
*Essential oil yield*.—0.2 mL/100 g cones.

The invention claimed is:

1. A new and distinct cultivar of hop plant named 'STUFF' substantially as illustrated and described herein.

* * * * *